United States Patent
Kim et al.

(10) Patent No.: US 10,724,061 B2
(45) Date of Patent: Jul. 28, 2020

(54) β-1,3-1,6-ENDOGLUCANASE PRODUCING, FROM β-GLUCAN, OLIGOSACCHARIDES OR GLUCOSE

(71) Applicant: KOREA UNIVERSITY RESEARCH AND BUSINESS FOUNDATION, Seoul (KR)

(72) Inventors: Kyoung Heon Kim, Seoul (KR); Damao Wang, Seoul (KR); Do-Hyoung Kim, Yongin-si (KR)

(73) Assignee: Korea University Research and Business Foundation, Seoul (KR)

( * ) Notice: Subject to any disclaimer, the term of this patent is extended or adjusted under 35 U.S.C. 154(b) by 0 days.

(21) Appl. No.: 16/096,351

(22) PCT Filed: Apr. 28, 2017

(86) PCT No.: PCT/KR2017/004591
§ 371 (c)(1),
(2) Date: Oct. 25, 2018

(87) PCT Pub. No.: WO2017/188788
PCT Pub. Date: Nov. 2, 2017

(65) Prior Publication Data
US 2020/0002738 A1 Jan. 2, 2020

(30) Foreign Application Priority Data
Apr. 29, 2016 (KR) .......... 10-2016-0053414

(51) Int. Cl.
C12P 19/02 (2006.01)
C12N 9/24 (2006.01)
C12N 15/52 (2006.01)
C12P 19/04 (2006.01)

(52) U.S. Cl.
CPC .......... *C12P 19/02* (2013.01); *C12N 9/2405* (2013.01); *C12N 15/52* (2013.01); *C12P 19/04* (2013.01)

(58) Field of Classification Search
None
See application file for complete search history.

(56) References Cited

U.S. PATENT DOCUMENTS 9,206,444 B2 * 12/2015 Brevnova .............. C12N 15/52

FOREIGN PATENT DOCUMENTS

KR 10-1483182 B1 1/2015

OTHER PUBLICATIONS

Weiner et al.,"Complete Genome Sequence of the Complex Carbohydrate-Degrading Marine Bacterium Saccharophagus degradans Strain 2-40 T", PLoS Genet 4(5): e1000087 (Year: 2008).*
Zverlov, Vladimir V., et al., "The binding pattern of two carbohydrate-binding modules of laminarinase Lam16A from Thermotoga neapolitana: differences in b-glucan binding within family CBM4", Microbiology, 2001, pp. 621-629, vol. 147, Great Britian (10 pages in English).
Shimokawa, Tomoko, et al., "Purification, Molecular Cloning, and Enzymatic Properties of a Family 12 Endoglucanase (EG-II) from Fomitopsis palustris: Role of EG-II in Larch Holocellulose Hydrolysis", Applied and Environmental Microbiology, Sep. 2008, vol. 74, No. 18, pp. 5857-5861 (6 pages in English).
Hutcheson. Steven W., et al., "Carbohydrase Systems of Saccharophagus degradans Degrading Marine Complex Polysaccharides", Marine Drugs, Apr. 2011, vol. 9, pp. 645-665 (22 pages in English).
Lafond, Mickael, et al., "Characterization of a Broad-Specificity β-Glucanase Acting on β-(1,3)-, β-(1,4)-, and β-(1,6)-Glucans That Defines a New Glycoside Hydrolase Family", Applied and Environmental Microbiology, Dec. 2012, vol. 78, No. 24, pp. 8540-8546 (8 pages in English).
NCBI Reference Sequence: WP_011469496.1, endoglucanase [Saccharophagus degradans], Jul. 11, 2013 (2 pages in English).
Miotto, Lis Schwartz, et al., "The Characterization of the Endoglucanase Cel12A from Gloeophyllum trabeum Reveals an Enzyme Highly Active on β-Glucan", PLOS One, Sep. 2014, vol. 9, No. 9, pp. 1-9 (10 pages in English).
International Serach Report dated Aug. 8, 2017 in corresponding International Application No. PCT/KR2017/004591 (3 pages in English, 4 pages in Korean).

* cited by examiner

Primary Examiner — Anand U Desai
(74) Attorney, Agent, or Firm — NSIP Law

(57) ABSTRACT

The present invention relates to a novel use of β-1,3-1,6-endoglucanase producing oligosaccharides or glucose from β-glucan. More specifically, the present invention provides an effect of producing oligosaccharides or glucose of various degrees of polymerization in high yields by using a β-1,3-1,6-endoglucanase exhibiting β-1,3-endoglucanase and ββ-1,6-endoglucanase activity on β-glucan and exhibiting transglycosylation activity on laminarioligosaccharide.

3 Claims, 14 Drawing Sheets

Specification includes a Sequence Listing.

β-1,3-1,6-ENDOGLUCANASE PRODUCING, FROM β-GLUCAN, OLIGOSACCHARIDES OR GLUCOSE

CROSS REFERENCE TO RELATED APPLICATION(S)

This application is a U.S. national stage application of International Application No. PCT/KR2017/004591 filed on Apr. 28, 2017, which claims the benefit of Korean Patent Application No. 10-2016-0053414 filed on Apr. 29, 2016, in the Korean Intellectual Property Office, the entire disclosures of which are incorporated herein by reference for all purposes.

BACKGROUND

1. Field of the Invention

The present invention relates to a novel β-1,3-1,6-endoglucanase producing an oligosaccharide or glucose from a β-glucan.

2. Discussion of Related Art

Currently, due to increased oil prices caused by the depletion of petroleum resources worldwide and strengthened environmental regulations according to strengthening of the United Nations Framework Convention on Climate Change (UNFCCC), research on the development of eco-friendly energy resources capable of replacing conventional fossil fuels such as petroleum, coal, etc. is actively progressing. Among these, brown algae consisting of a variety of polysaccharides grow more quickly than lignocellulosic and herbaceous biomass and have an advantage of high productivity per cultivated area. In addition, since brown algae has a low lignin content, the conversion to raw materials for producing bioenergy and chemicals is easy, and since carbon dioxide in the air is absorbed through photosynthesis, brown algae are in the spotlight as a resource for producing eco-friendly and economical bioenergy and chemicals.

Brown algae comprise alginate, fucoidan, mannitol, laminarin, and etc. and brown algae-derived polysaccharides contain a very high ratio of laminarin according to the species of brown algae. For example, *Laminaria hyperborean* and *Saccharina latissimi* contain laminarin at approximately 32% of their dry weight, and approximately 85% of total carbohydrates in *Fucus vesiculosus* is laminarin. Laminarin has a backbone with mainly β-1,3-glycosidic bonds and some β-1,6-glycosidic bonds. For effective saccharification of laminarin, glycoside hydrolases (GHs) are needed to cleave the glycosidic bonds, and the β-1,3-glucanases are classified into two major groups according to enzymatic properties. A β-1,3-endoglucanase cleaves internal β-1,3 glycosidic bonds, thereby producing various oligosaccharides, and a β-1,3-exoglucanase is known to produce glucose from non-reducing ends. The final product, glucose, produced through such an enzymatic reaction can be used as a raw material suitable for producing biofuels such as ethanol, etc., and a laminarioligosaccharide, which is produced by the enzymatic reaction, also can be used as a useful, physiologically active material.

In terms of the β-1,3-endoglucanase, Korean Patent No. 10-1483182 discloses that laminarin is degraded into glucose and laminaribiose by the β-1,3-endoglucanase, but reactivity of the enzyme with respect to pustulan is not disclosed.

SUMMARY OF THE INVENTION

The present invention is directed to provide the use of a novel β-1,3-1,6-endoglucanase which can produce an oligosaccharide or glucose from a β-glucan.

To achieve the object, the present invention provides a composition for producing an oligosaccharide or glucose, which includes a β-1,3-1,6-endoglucanase represented by the amino acid sequences set forth in SEQ ID NO: 1, and including one or more selected from the group consisting of laminarin, pustulan and a laminarioligosaccharide as a substrate.

The present invention also provides a method of producing an oligosaccharide or glucose, which includes reacting a β-1,3-1,6-endoglucanase represented by the amino acid sequences set forth in SEQ ID NO: 1 with one or more substrate selected from the group consisting of laminarin, pustulan and a laminarioligosaccharide.

There is an effect that the present invention provides a β-1,3-1,6-endoglucanase exhibiting β-1,6-endoglucanase activity as well as β-1,3-endoglucanase activity with respect to a β-glucan and having transglycosylation activity with respect to a laminarioligosaccharide.

The β-1,3-1,6-endoglucanase can use laminarin, pustulan, and a laminarioligosaccharide as substrates, and thus provides an effect of producing oligosaccharides with a variety of degrees of polymerization or glucose at a high yield.

DETAILED DESCRIPTION OF EXEMPLARY EMBODIMENTS

Figure 1:
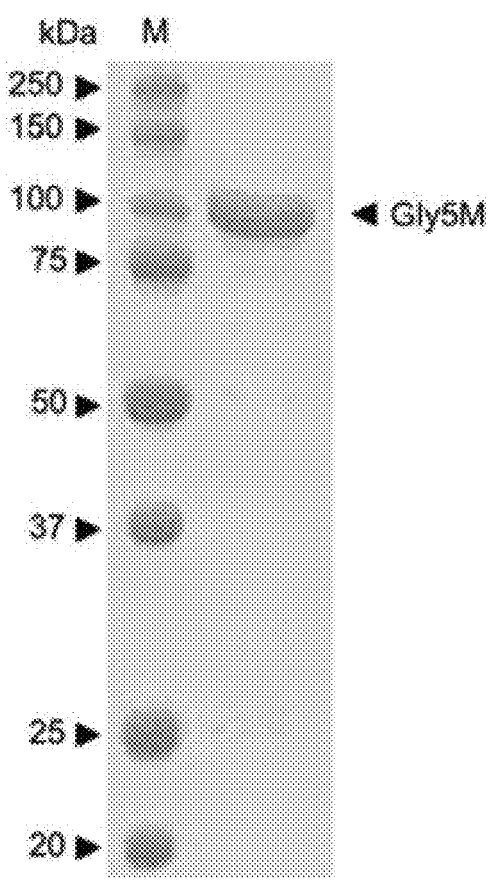
FIG. 1 is a gel image that identifies the expression of a β-1,3-1,6-endoglucanase according to the present invention.

The inventors identified the β-glucanase activity of the Gly5M protein belonging to the GH5 family which is assumed to have β-glycosidase activity. As a result, it was found that the Gly5M protein cleaved β-1,3-glycosidic bonds of laminarin as a substrate, which is a polysaccharide consisting of β-1,3-linked glucose main chain and β-1,6-linked glucose branches, thereby producing a laminarioligosaccharide and glucose, and cleaved β-1,6-glycosidic bonds of a substrate, pustulan, which is a polysaccharide consisting of glucose monomers linked by β-1,6-bonds, thereby producing a gentio-oligosaccharide and glucose. It was also confirmed that, when the laminarioligosaccharide is used as a substrate, the Gly5M protein exhibited transglycosylation activity, and thus produced an oligosaccharide having a higher DP value than the laminarioligosaccharide as a substrate. Since the various enzymatic properties of the Gly5M protein include the β-1,3-endoglucanase activity which is not shown in other enzymes belonging to the GH5 family, new information on GH5 family enzymes, that was previously unknown, was provided.

Therefore, the present invention provides a composition for producing an oligosaccharide or glucose, which includes a β-1,3-1,6-endoglucanase represented by the amino acid sequences set forth in SEQ ID NO: 1, in which the β-1,3-1,6-endoglucanase uses one or more selected from the group consisting of laminarin, pustulan and a laminarioligosaccharide as a substrate.

In addition, the present invention provides a method of producing an oligosaccharide or glucose, which includes reacting a β-1,3-1,6-endoglucanase represented by an amino acid sequence set forth in SEQ ID NO: 1 with one or more substrate selected from the group consisting of laminarin, pustulan and a laminarioligosaccharide.

The β-1,3-1,6-endoglucanase exhibits β-1,3-endoglucanase and β-1,6-endoglucanase activities with respect to a β-glucan, and transglycosylation activity with respect to a laminarioligosaccharide.

The β-1,3-1,6-endoglucanase maintains thermal stability up to approximately 20 to 45° C., and exhibits the optimum degrading activity with respect to laminarin, a laminarioligosaccharide or pustulan. More specifically, the optimum activities may be exhibited at approximately 30 to 40° C.

In addition, the optimum pH of the β-1,3-1,6-endoglucanase in a buffer may vary according to the type of buffer, but may range from approximately pH 4 to 10, more specifically, approximately pH 4 to 9, and most specifically approximately pH 6.

The β-1,3-1,6-endoglucanase may use laminarin, pustulan and a laminarioligosaccharide as a substrate.

The laminarioligosaccharide used as a substrate is more specifically any one of laminarioligosaccharides having a degree of polymerization (DP) of 2 to 6. For example, the laminarioligosaccharide may be laminaribiose (DP2), laminaritriose (DP3), laminaritetraose (DP4), laminaripentaose (DP5), or laminarihexaose (DP6). When any one of the laminarioligosaccharides with a DP of 2 to 6 is used as a substrate, a laminarioligosaccharide showing a peak indicating a higher DP value than that of the substrate due to the transglycosylation activity may be obtained as a degradation product.

In addition, the reaction product of the enzyme may be a laminarioligosaccharide, a gentio-oligosaccharide, or glucose.

The laminarioligosaccharide may be any one of the laminarioligosaccharides having degrees of polymerization of 2 to 17. More specifically, a large quantity of laminaribiose, laminaritriose, laminaritetraose, laminaripentaose or laminarihexaose with a degree of polymerization of 2 to 6 may be produced.

The gentio-oligosaccharide may be any one of gentio-oligosaccharides having degrees of polymerization of 2 to 8. More specifically, a large quantity of gentiobiose with a degree of polymerization of 2 may be produced.

The β-1,3-1,6-endoglucanase may be derived from *Saccharophagus degradans* 2-40$^T$, but the present invention is not particularly limited thereto.

In addition, the β-1,3-1,6-endoglucanase may be transcribed and translated from a DNA fragment, that is, a coding gene, associated with the production of a polypeptide not only including upstream and downstream regions of the coding region of the enzyme, but also including an intron between individual coding fragments. For example, the β-1,3-1,6-endoglucanase may be transcribed and translated from the sequences set forth in SEQ ID NO: 2, but the present invention is not particularly limited thereto. In addition, a protein having an oligosaccharide or glucose hydrolytic activity as a mutant protein derived from the enzyme with one or more substitutions, deletions, translocations and additions, is also included in the scope of the enzyme of the present invention, and the protein preferably includes an amino acid sequence having at least 80%, 85%, 90%, 93%, 94%, 95%, 96%, 97%, 98%, or 99% sequence identity with the amino acid sequence set forth in SEQ ID NO: 1.

The β-1,3-1,6-endoglucanase may be isolated and purified from a supernatant of a *Saccharophagus degradans* 2-40$^T$ culture, or may be produced and isolated by using a strain other than the *Saccharophagus degradans* 2-40$^T$ by a genetic-engineering recombination technique, or by an artificial, chemical synthesis method.

When the recombination technique is used, factors used to facilitate conventional recombinant protein expression, for example, an antibiotic resistance gene, and a reporter protein or peptide which can be used in affinity column chromatography, may be used, and this technique is included in the range that can be easily embodied by those of ordinary skill in the art to which the present invention belongs. For example, the β-1,3-1,6-endoglucanase may be obtained from host cells transformed with a recombinant vector comprising a gene encoding the β-1,3-1,6-endoglucanase, that is, the base sequences set forth in SEQ ID NO: 2, or the culture thereof. The host cells may be *Escherichia coli*, but the present invention is not limited thereto.

The reaction between the β-1,3-1,6-endoglucanase and the substrate may be performed at a temperature ranging from 20 to 45° C. and a pH ranging from 5 to 10 for 5 minutes to 1 day. More specifically, when laminarin or pustulan is used as a substrate, the reaction may be performed at a temperature ranging from 38 to 42° C. and a pH ranging from 5 to 7 for 5 minutes to 5 hours. When a laminarioligosaccharide is used as a substrate, the reaction may be performed at a temperature ranging from 38 to 42° C. and a pH ranging from 5 to 7 for 1 to 5 hours.

The degradation product of the enzyme may be sequentially subjected to silica gel chromatography, which is adsorption chromatography, and biogel P2 chromatography, which is gel permeation chromatography, to isolate and purify an oligosaccharide or glucose with a high purity of approximately 95%.

The "protein" and "polypeptide" used herein are used interchangeably.

In the present invention, the expression "a polypeptide has a specific percentage (e.g., 80%, 85%, 90%, 95% or 99%) of sequence identity with another sequence" means that, when two sequences are aligned and compared, the specific percentage of amino acid residues are the same. The alignment and percent homology or identity may be determined using suitable software programs known in the art, for example, the methods disclosed in the literature [CURRENT PROTOCOLS IN MOLECULAR BIOLOGY (F. M. Ausubel et al., (eds) 1987 Supplement 30 section 7.7.18)]. Preferable programs that can be used herein include the GCG Pileup program, FASTA (Pearson et al., 1988 *Proc. Natl Acad. Sci USA* 85:2444-2448), and BLAST (BLAST Manual, Altschul et al., Natl. Cent. Biotechnol. Inf., Natl Lib. Med. (NCIB NLM NIH), Bethesda, Md., and Altschul et al., 1997 NAR25:3389-3402). Another preferable alignment program is ALIGN Plus (Scientific and Educational Software, PA), preferably using basic parameters. Another available sequence software program is the TFASTA Data Searching Program available in Sequence Software Package Version 6.0 (Genetics Computer Group, University of Wisconsin, Madison, Wis.).

The term "recombinant" used herein means that, when being used in relation to a cell, nucleic acid, protein or vector, the cell, nucleic acid, protein or vector has been modified by introduction of a heterologous nucleic acid or protein or a change in an intrinsic nucleic acid or protein, or the cell is derived from a cell modified in such a manner. In other words, a recombinant cell expresses a gene which is not found in an intrinsic (non-recombinant) form of the cell, or alternatively, expresses an intrinsic gene which is abnormally expressed or never expressed.

The "nucleic acid" used herein encompasses single- or double-stranded DNA, RNA, and chemically-modified forms thereof. The "nucleic acid" and "polynucleotide" used herein can be used interchangeably. Due to the degeneracy of a genetic code, one or more codons may be used to encode a specific amino acid, and the present invention encompasses a polynucleotide encoding a specific amino acid sequence.

The term "introduction" used herein to describe the insertion of a nucleic acid sequence into a cell refers to "transfection," "transformation" or "transduction," and includes the description of incorporation of a nucleic acid sequence into a eukaryotic or prokaryotic cell. At this time, the nucleic acid sequence is incorporated into the genome of the cell (e.g., chromosomal, plasmid, plastid or mitochondrial DNA), and thus is converted into an autonomous replicon, or transiently expressed.

Hereinafter, the present invention will be described in further detail with reference to examples according to the present invention, but the scope of the present invention is not limited to the following examples.

<Example 1> Acquisition of gly5m Gene by Cloning Technique

*Saccharophagus degradans* 2-40$^T$ was cultured in a minimal medium containing 23 g/L of instant ocean sea salt, 50 mM Tris-HCl, 2 g/L of glucose, 2 g/L of yeast extract and 0.5 g/L of ammonium chloride at 30° C. for 12 hours.

The genomic DNA of *Saccharophagus degradans* 2-40$^T$ (ATCC 43961) was obtained using a commercially available DNA isolation kit (Qiagen, Valencia, Calif., USA). The target gene, gly5m (GeneBank ID. ABD82251.1), was amplified using Solg 2×Taq PCR Smart mix 2 (SolGent, Daejeon, Korea). Primers used herein were 5'-GCGGGATC-CATGAGAGAAAAACTACTGCGCG-3' (forward) (SEQ ID NO: 3) and 5'-GCGCTCGAGGTGGTGGTGGTGGTG-GTGGTCAACTGCTTCAACACTCCA-3' (reverse)(SEQ ID NO: 4) , each of which having BamHI and XhoI restriction sites at the 5' end. In addition, to increase the affinity of a HisTrap column, the base sequence of a gene encoding histidine was added. Both of a PCR product and a pET28a+ vector were double digested with BamHI and XhoI, and the final DNA fragments were ligated. The gly5m-haboring plasmid was transformed into *Escherichia coli* DH5α.

<Example 2> Overexpression and Purification of Gly5M

For overexpression of the gene acquired in Example 1, the gene was transformed into a protein-expressing host, *Escherichia coli* B121 (DE3). The bacterial cells were cultured in Luria-Bertani (LB) broth (BD, Sparks, Md., USA) containing 50 mg/L of kanamycin at 37° C. until the absorbance at 600 nm reached 0.6. The protein expression was induced using 0.1 mM IPTG at 16° C., and therefore a recombinant protein was expressed in a water-soluble type. For isolation of the expressed Gly5M protein, the cells were disrupted by ultrasonication and centrifuged, followed by purification of the supernatant using a HisTrap column (GE Healthcare, Piscataway, USA). The purified protein was concentrated using an Amicon Ultra Centrifugal filter (Millipore, Billerica, Mass., USA), and the concentration of the protein was measured using a bicinchoninic acid (BCA) protein assay kit (Pierce, Rockford, Ill., USA).

The molecular weight of the expressed Gly5M was measured as approximately 95 kDa using SDS-PAGE (FIG. 1).

<Example 3> Confirmation of Substrate Specificity and Cationic Effect of Gly5M

To confirm the substrate specificity of the Gly5M protein, 1% of various glucans including pustulan, laminarin, curdlan (Wako, Osaka, Japan), carboxymethylcellulose (Sigma-Aldrich, St Louis, Mo., USA), and xylan (Sigma-Aldrich, St Louis, Mo., USA), contained in a 20 mM Tris-HCl (pH 6.0), were reacted with 10.5 μM of the Gly5M protein at 40° C. for 30 minutes. The produced reducing sugars were quantified by a DNS method.

As shown in Table 1, the Gly5M protein exhibited the highest activity with respect to laminarin, and when pustulan was used as a substrate, compared with when laminarin was solely used as a substrate, the Gly5M protein exhibited a relative activity of approximately 55.6%. It was confirmed that the Gly5M protein does not hydrolyze curdlan, unlike other β-glucanases, which is very similar to the characteristic of a β-1,3-glucanase which is highly active in curdlan, compared with the case using laminarin. It was also confirmed that the Gly5M protein does not react at β-1,4-glycosidic bonds in Avicel®, a barley β-glucan, CM-cellulose and Xylan.

As a result of confirming the cationic effect of the Gly5M protein, as shown in Table 2, it was seen that the reactivity of the Gly5M protein is inhibited by cations such as $Ni^{2+}$, $Cu^{2+}$, $Fe^{2+}$, and $Co^{2+}$.

TABLE 1

| Substrate | Glycosidic bond | Relative enzyme activity (%) |
| --- | --- | --- |
| Laminarin | β-1,3 and β-1,6 (glucose) | 100.0 |
| Pustulan | β-1,6 (glucose) | 55.6 |
| Curdlan | β-1,3 (glucose) | ND |
| β-glucan (barley) | β-1,3 and β-1,4 (glucose) | ND |
| Xylan | β-1,4 (xylose) | ND |

TABLE 1-continued

| Substrate | Glycosidic bond | Relative enzyme activity (%) |
|---|---|---|
| Avicel ® | β-1,4 (glucose) | ND |
| Carboxymethyl cellulose | β-1,4 (glucose) | ND |

ND means undetected.

TABLE 2

| Cation | Relative activity (%) |
|---|---|
| Control | 100.2 ± 0.9 |
| $K^+$ | 99.1 ± 1.4 |
| $Na^+$ | 100.3 ± 1.4 |
| $Mg^{2+}$ | 63.1 ± 1.2 |
| $Ca^{2+}$ | 103.4 ± 2.9 |
| $Mn^{2+}$ | 101.7 ± 0.8 |
| $Ni^{2+}$ | 22.5 ± 1.2 |
| $Cu^{2+}$ | 25.3 ± 0.2 |
| $Fe^{2+}$ | 20.7 ± 1.1 |
| $Co^{2+}$ | 56.8 ± 0.7 |

Activity without cations was set as 100%.
Experimental data is expressed as mean ± standard deviation from triplicate experiments <Example 4> Confirmation of Optimal pH and Activation Temperature of Gly5M To investigate the optimal pH with respect to the activity of the Gly5M protein, 2% laminarin contained in 20 mM glycine-HCl (pH 2.0 to 4.0), 20 mM sodium acetate (pH 4.0 to 6.0), 20 mM Tris-HCl (pH 6.0 to 9.0), and 20 mM glycine-NaOH (pH 9.0 to 10.0) were reacted with the Gly5M protein.

Figure 2:
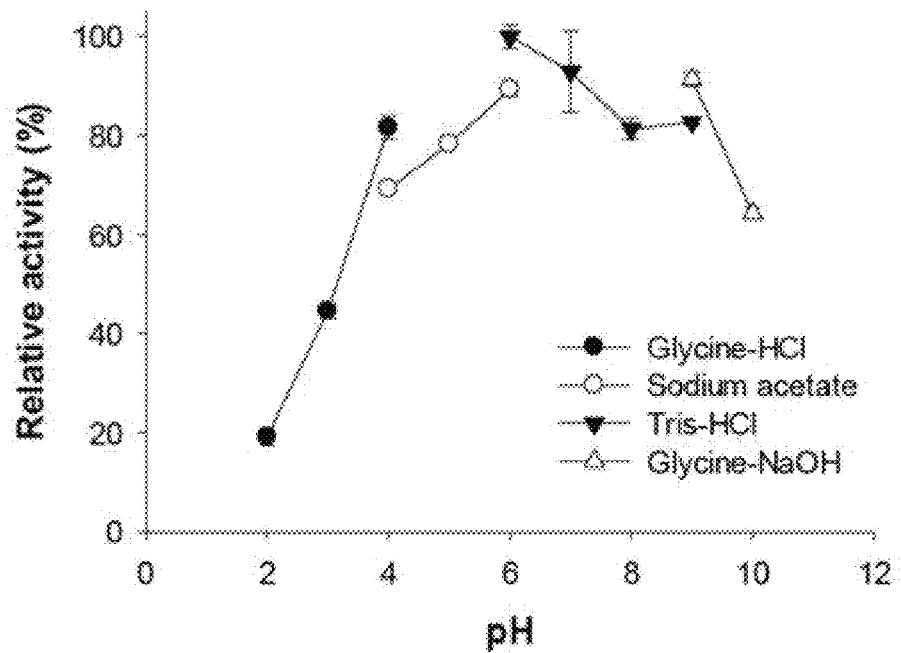
FIG. 2 is the results for identifying the optimal activity pH for a β-1,3-1,6-endoglucanase of the present invention.

FIG. 2 shows the relative activity of Gly5M at a pH ranging from 2.0 to 10.0. It was confirmed that Gly5M exhibited the highest activity at a pH 6.0, and is drastically decreased in enzymatic activity at a pH slightly less than or higher than the pH 6.0.

To investigate the optimal temperature with respect to the activity of the Gly5M protein, 2% laminarin contained in 20 mM Tris-HCl was reacted with Gly5M.

Figure 3:
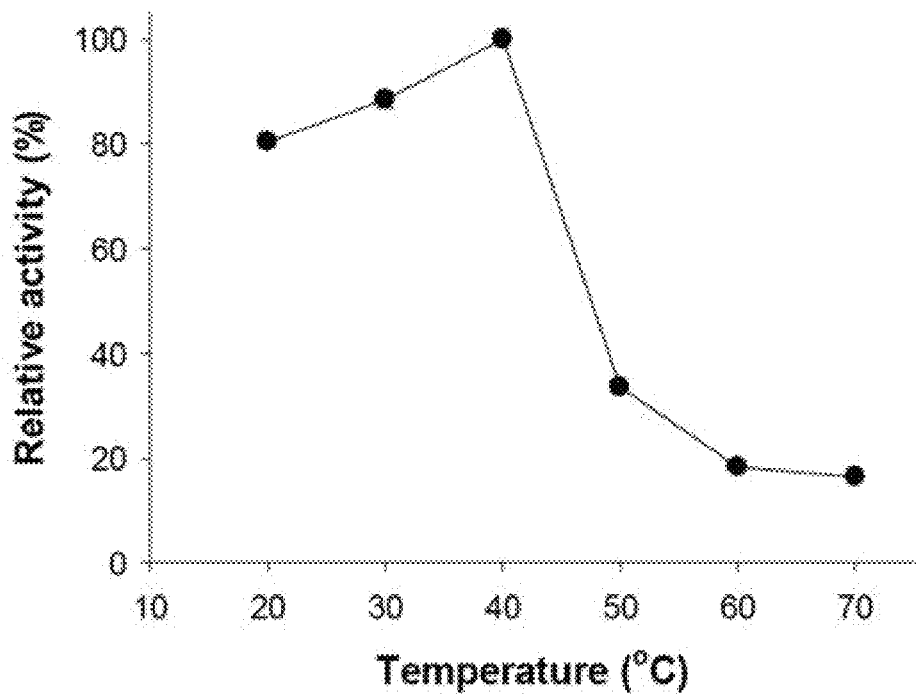
FIG. 3 is the results for identifying the optimal activity temperature for a β-1,3-1,6-endoglucanase of the present invention.

FIG. 3 shows the relative activity of Gly5M at a temperature ranging from 20 to 70° C. As the temperature increases in a range of 20 to 40° C., the enzymatic activity gradually increased and reached its highest value at 40° C. The enzymatic activity from the reaction temperature of 40° C. drastically decreased, compared with that observed at 40° C.

Figure 4:
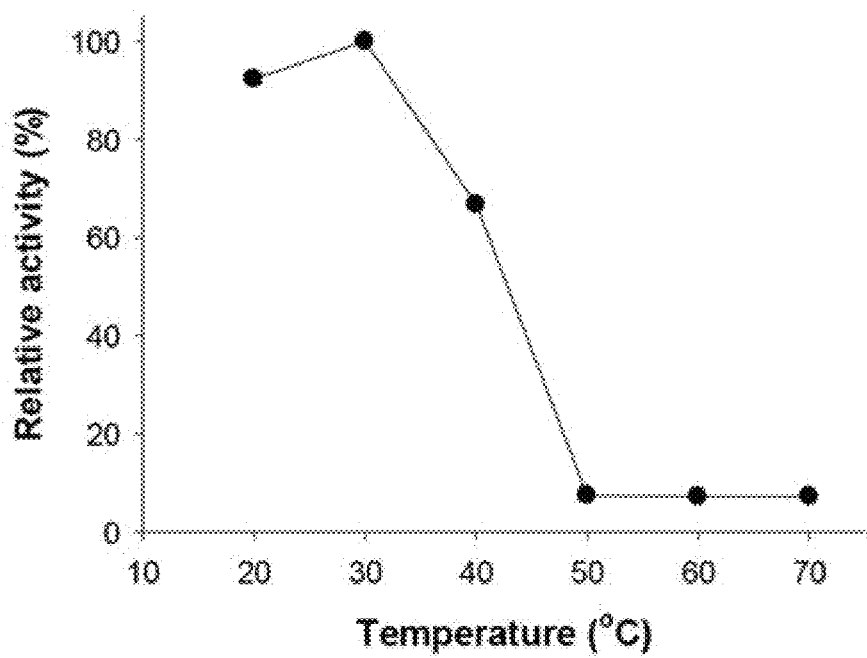
FIG. 4 is the results for confirming the thermal stability of a β-1,3-1,6-endoglucanase of the present invention.

To confirm the thermal stability of Gly5M, when the reaction was performed at a temperature higher than 40° C. for 1 hour, compared with the stability of Gly5M reacted at 40° C. for 1 hour, it was confirmed that the relative activity was drastically decreased (see FIG. 4). Therefore, the optimal reaction temperature of Gly5M was determined to be 30° C., which was applied in all subsequent experiments.

<Example 5> Confirmation of Enzymatic Reaction Rate of Gly5M

To confirm the enzymatic reaction rate of the Gly5M protein with respect to laminarin, laminarin which was contained at various concentrations of 0.45-9.1% in 20 mM Tris-HCl buffer was reacted with the protein at pH 6.0 and 40° C.

Figure 5:
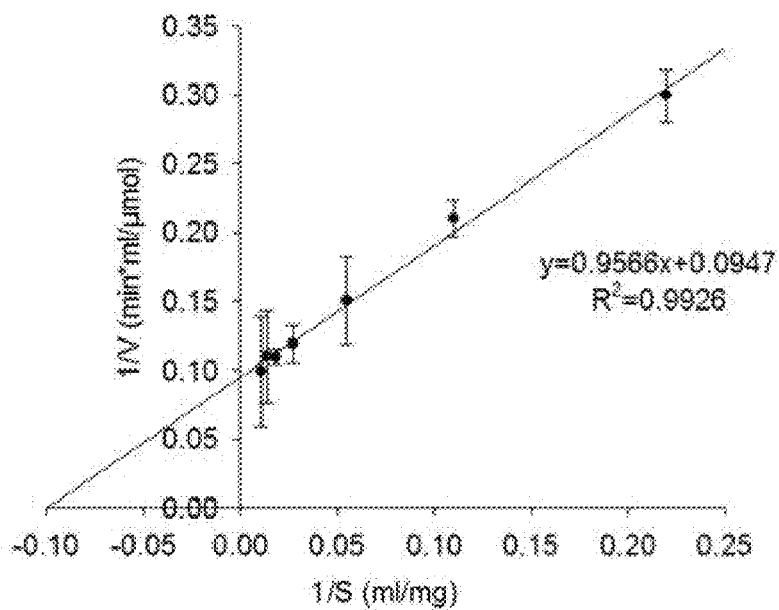
FIG. 5 illustrates a Lineweaver-Burk plot of a β-1,3-1,6-endoglucanase of the present invention with respect to the hydrolysis of laminarin as a substrate.

As a result, from the Lineweaver-Burk plot (see FIG. 5), $K_m$, $V_{max}$ and $K_{cat}$ values were determined to be 10.4 g/L, 10.6 U/mg and 16.8 $s^{-1}$, respectively.

<Example 6> Confirmation of Characteristics of Enzymatic Reaction of Gly5M Protein Using TLC and HPLC Characteristics of the enzymatic reaction of the Gly5M protein over time were analyzed using thin layer chromatography (TLC) and high performance liquid chromatography (HPLC).

A reaction product for the TLC analysis was developed on a silica gel 60 plate (Merck) using a n-butanol:acetic acid:water (3:2:2 by volume) mixed solvent system, visualized by treatment with 10% (v/v) sulfuric acid, and then heat-treated at 130° C. for 5 minutes.

HPLC analysis was performed using an Agilent 1100 HPLC (Agilent) equipped with a gel permeation and ligand exchange column (KS-802; Shodex), and detected using a refractive index detector (Agilent). A solvent for the HPLC analysis was distilled water, a flow rate was 0.5 mL/min, and a column temperature was set to be 80° C. Standard materials for the analysis include laminaribiose (DP2), laminaritriose (DP3), laminaritetraose (DP4), laminaripentaose (DP5), and laminarihexaose (DP6), all purchased from Megazyme.

Figure 6A:
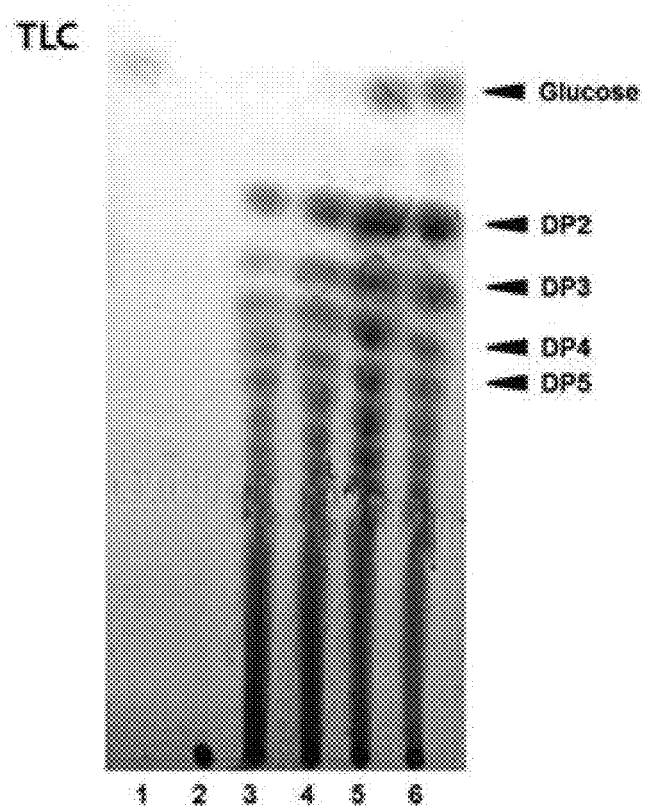
FIG. 6 is the results of TLC (a) and HPLC (b) analyses of a reaction product of a β-1,3-1,6-endoglucanase of the present invention using laminarin as a substrate.

As a result of the TLC analysis of the products obtained from the reaction between the Gly5M protein and laminarin (see FIG. 6a), it was confirmed that oligosaccharides showing various DP values are produced 5 or more minutes after the reaction, and it was also confirmed that large quantities of oligosaccharides having low DP values corresponding to DP2 to DP5 and glucose are produced over time.

Figure 6B:
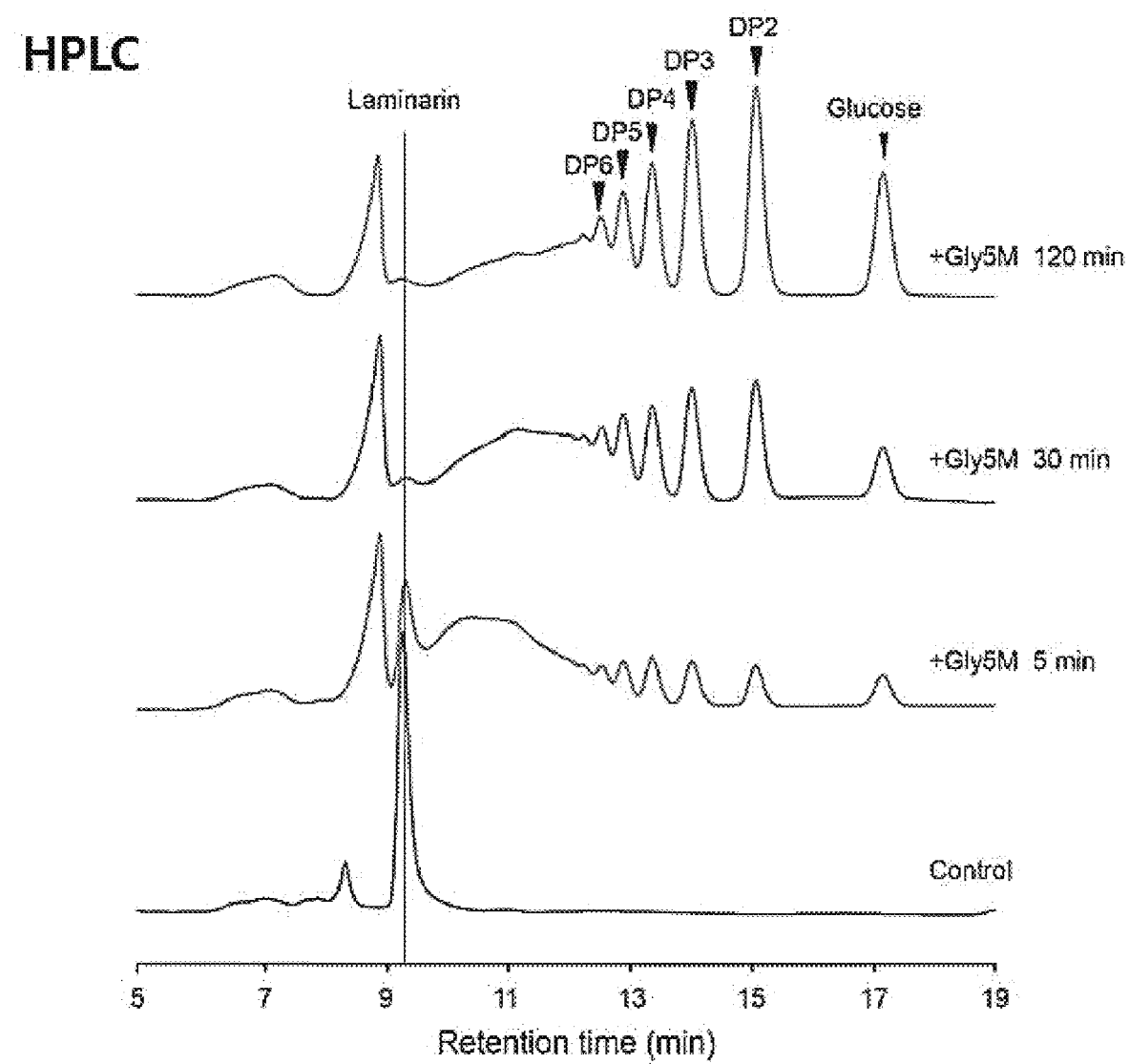

As a result of the HPLC analysis for the same reaction products (see FIG. 6b), it was confirmed that the number of peaks indicating DP values lower than DP5 increases over time. This result shows that the Gly5M protein randomly cleaves β-1,3-glycosidic bonds in laminarin.

Figure 7A:
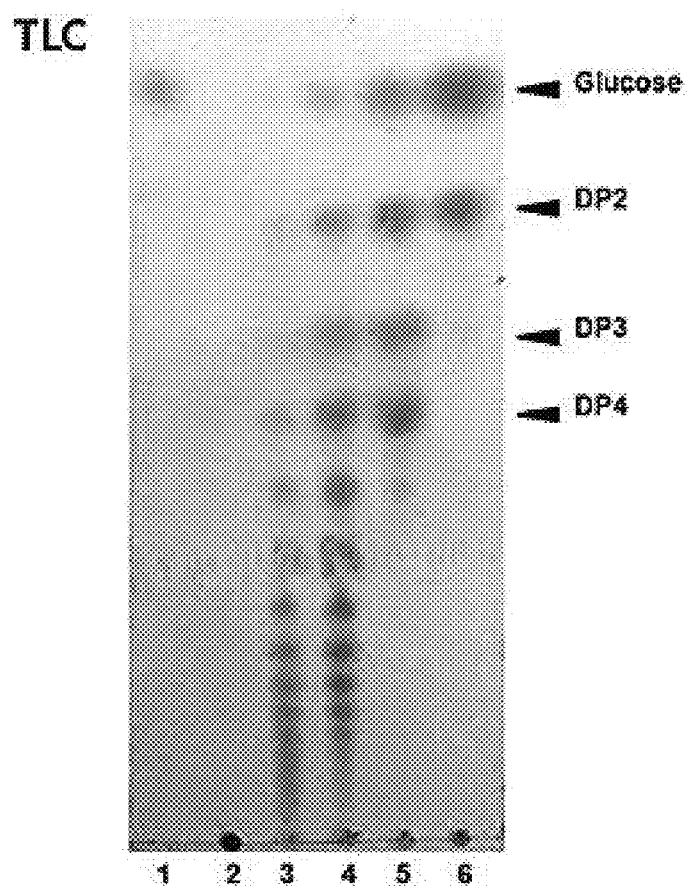
FIG. 7 is the results of TLC (a) and HPLC (b) analyses of a reaction product of a β-1,3-1,6-endoglucanase of the present invention using pustulan as a substrate.
Figure 7B:
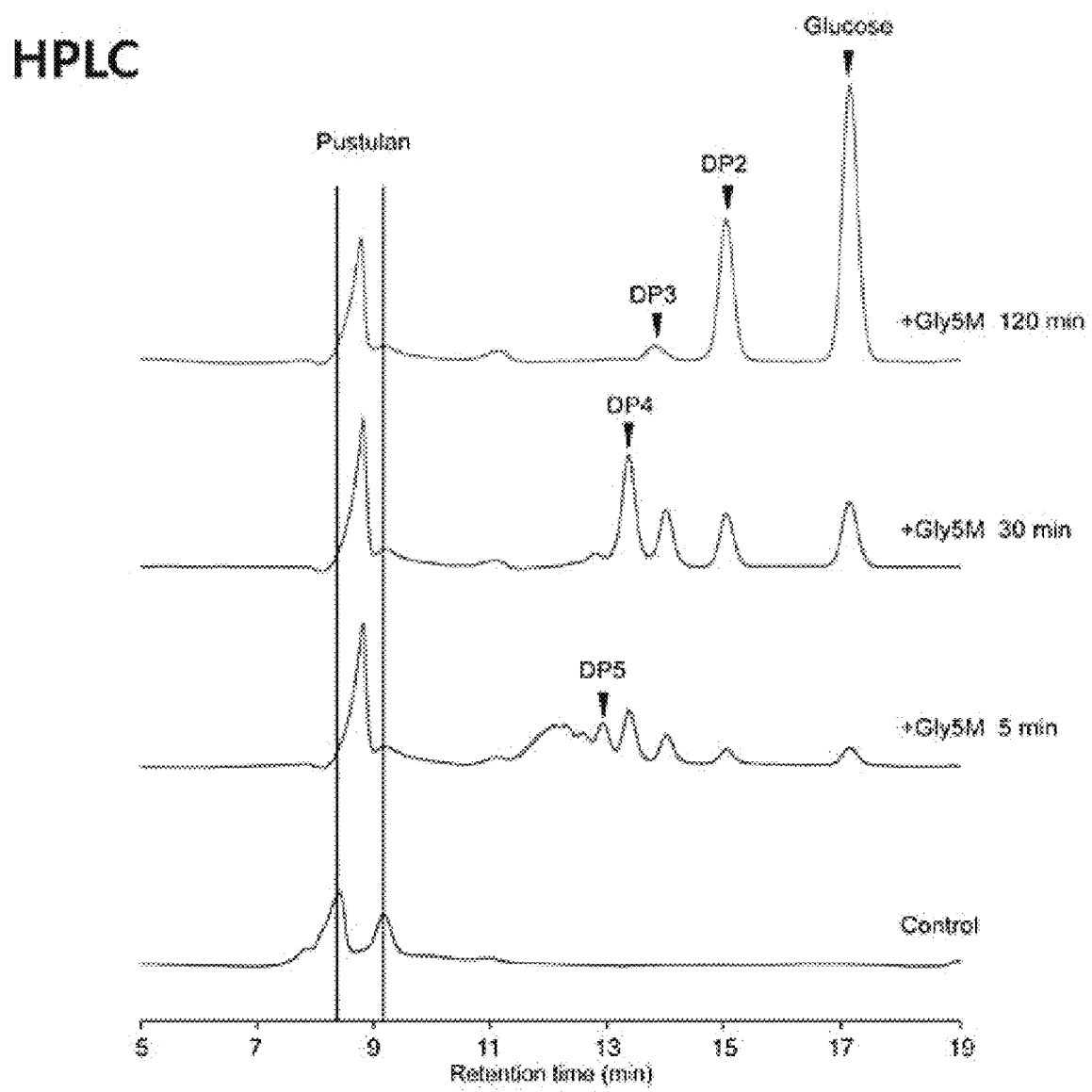

It was confirmed that, when the Gly5M protein is reacted with pustulan, in the early stage, oligosaccharides with various DP values are produced, but ultimately, large amounts of gentiobiose (DP2) and glucose are produced (see FIGS. 7a and 7b).

<Example 7> Confirmation of Characteristics of Enzymatic Reaction of Gly5M Protein Using MALDI-TOF/TOF MS To further confirm the characteristics of the enzymatic reaction of the Gly5M protein, matrix-assisted laser desorption ionization-tandem time of flight mass spectrometry (MALDI-TOF/TOF MS) analysis was performed using laminarin, pustulan and a laminarioligosaccharide as substrates for 2 hours. Each sample for the analysis was mixed with 0.3 µL of 0.01M NaCl, and 0.5 µL of 50 g/L 2,5-dihydroxybenzoate dissolved in 50% (v/v) acetonitrile, and then spotted onto a stainless-steel target plate. The spotted sample was rapidly dried for crystallization and analyzed using an ultraFlextreme MALDI-TOF/TOF MS system (Bruker Daltonics). Raw MS data was processed using FlexAnalysis software (version 3.3; Bruker Daltonics).

Figure 8A:
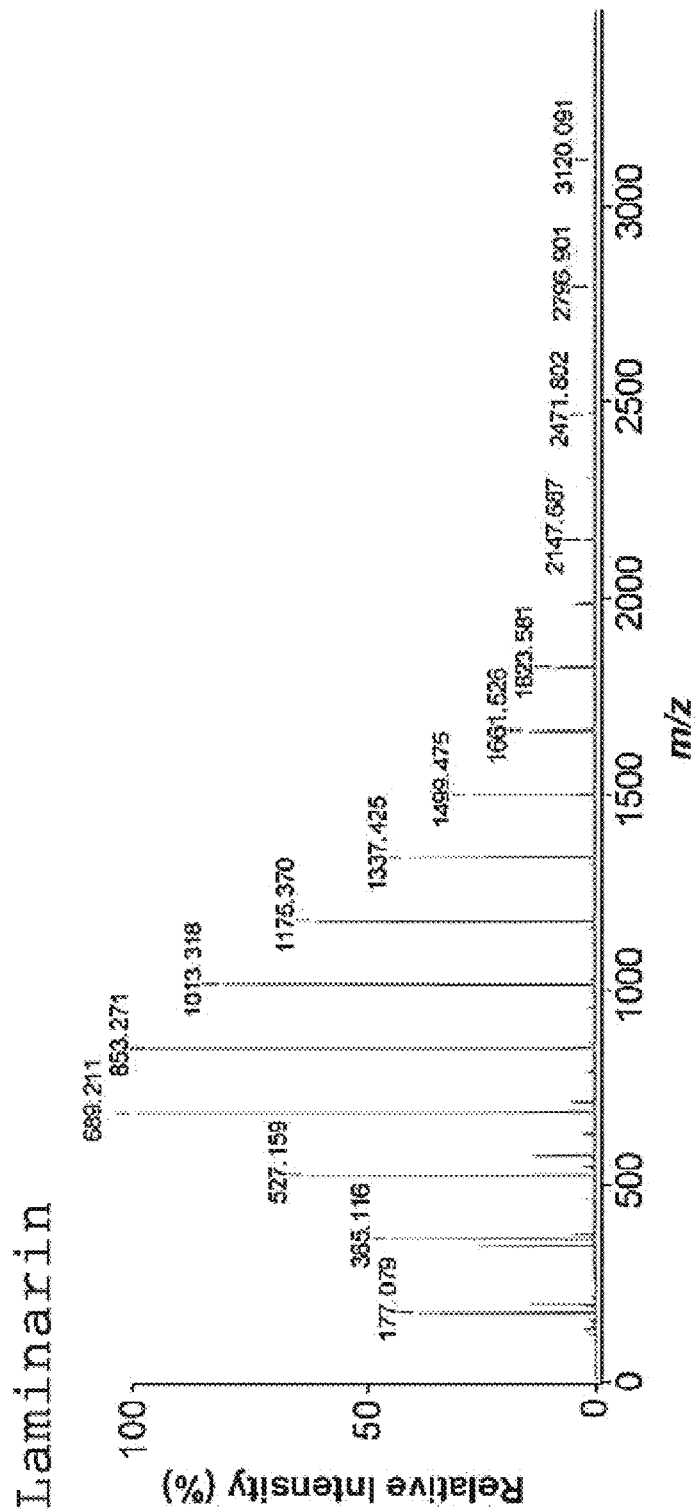
FIG. 8 is the results of MALDI-TOF/TOF MS analyses of a reaction product of a β-1,3-1,6-endoglucanase of the present invention using laminarin (a) and pustulan (b) as substrates.

It was confirmed that, when laminarin was used as a substrate, most of the substrate was converted into glucose by the Gly5M protein, and other than glucose, DP4 and DP5 of various oligosaccharides ranging from DP2 to DP17 were mainly produced (see FIG. 8a).

Figure 8B:
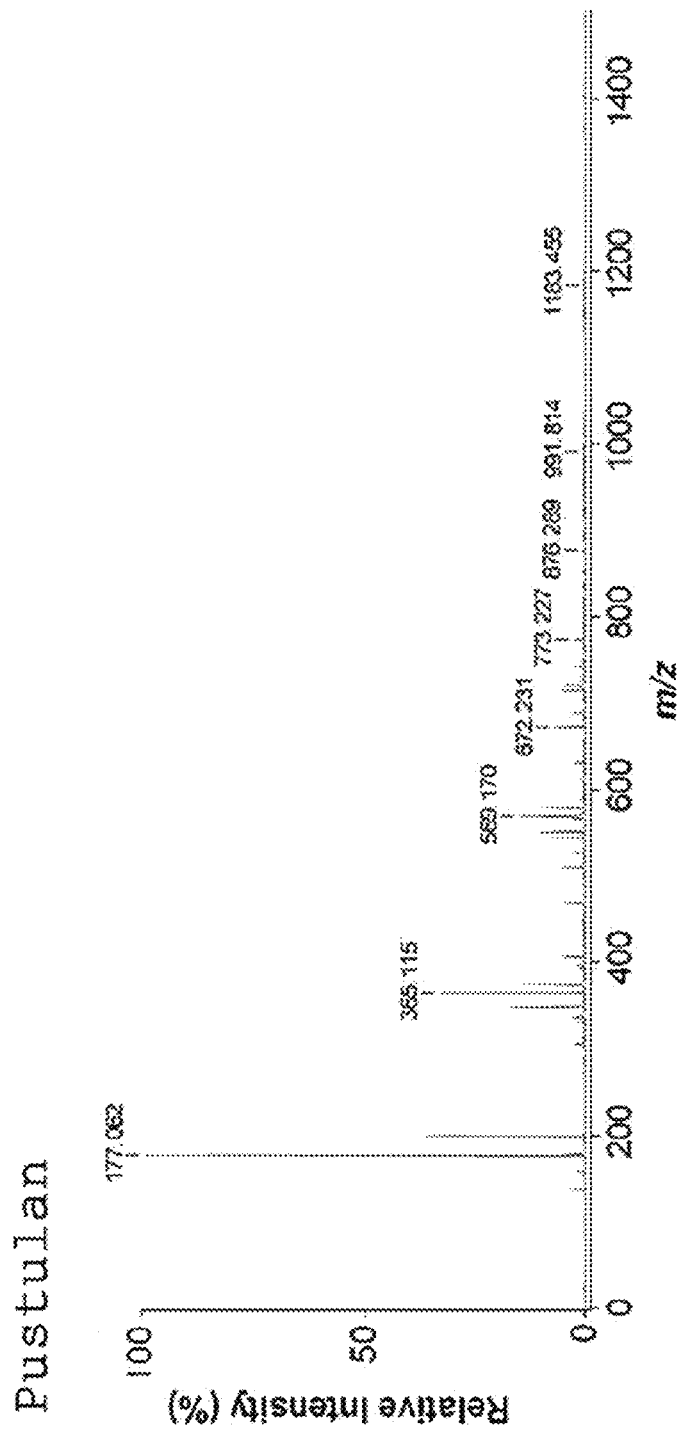
Figure 9:
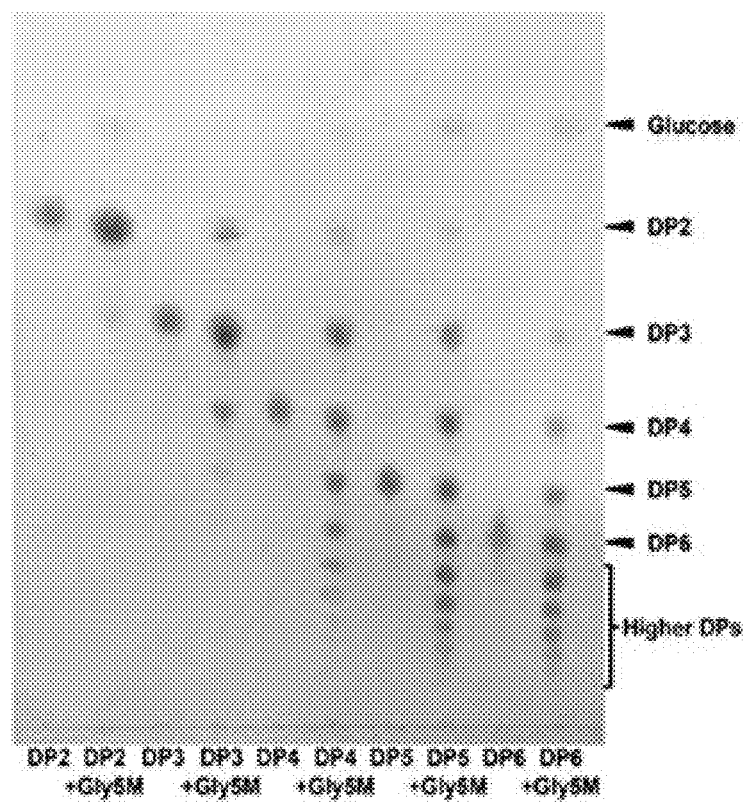
FIG. 9 is the result of TLC analysis of a β-1,3-1,6-endoglucanase of the present invention using a laminarioligosaccharide as a substrate.
Figure 10A:
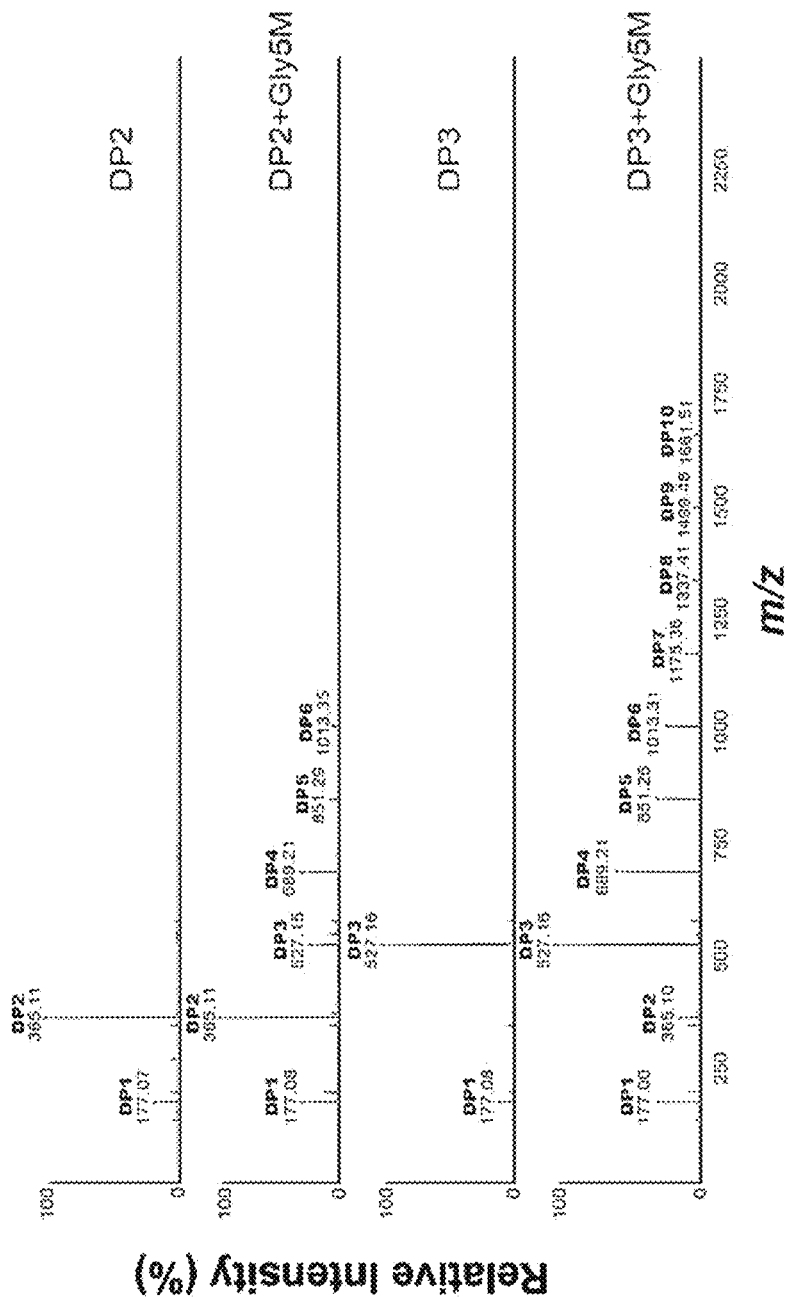
FIGS. 10a to 10c are the results of MALDI-TOF/TOF MS analyses of a β-1,3-1,6-endoglucanase of the present invention using a laminarioligosaccharide as a substrate.
Figure 10B:
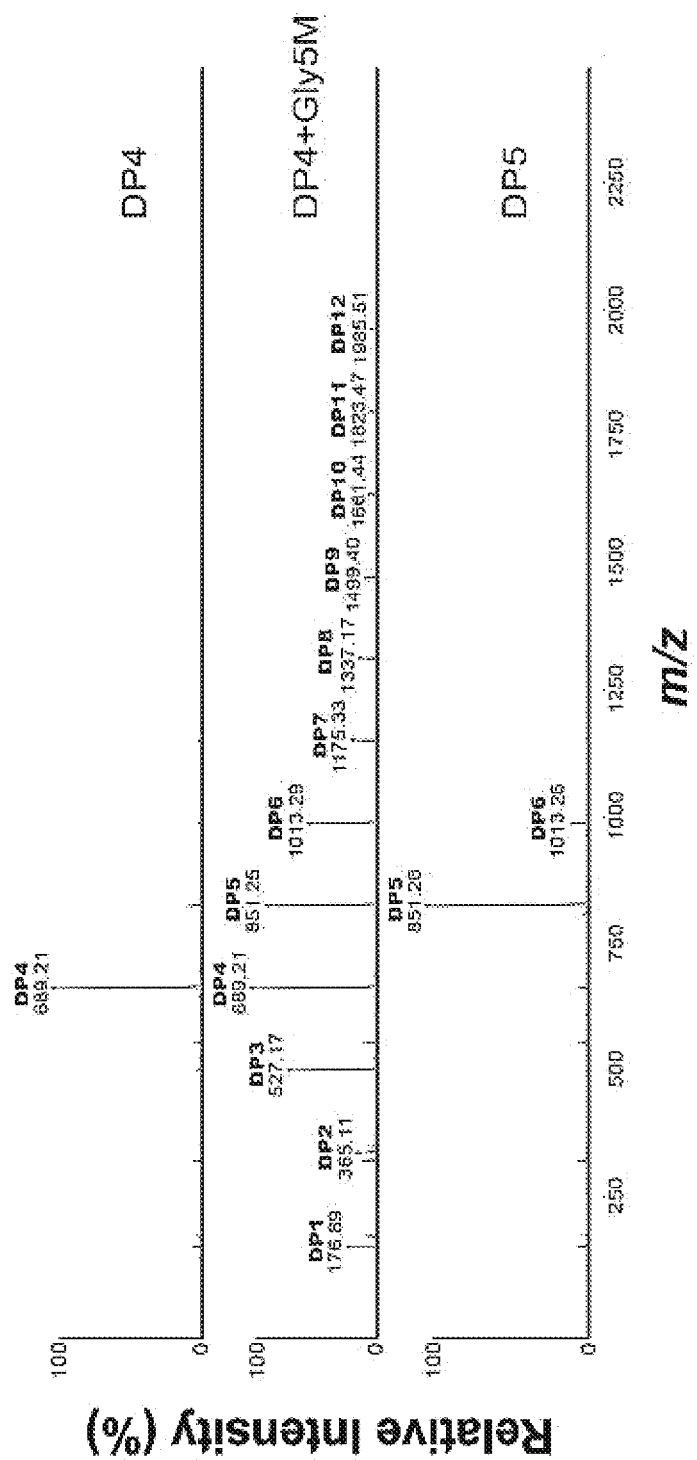
Figure 10C:
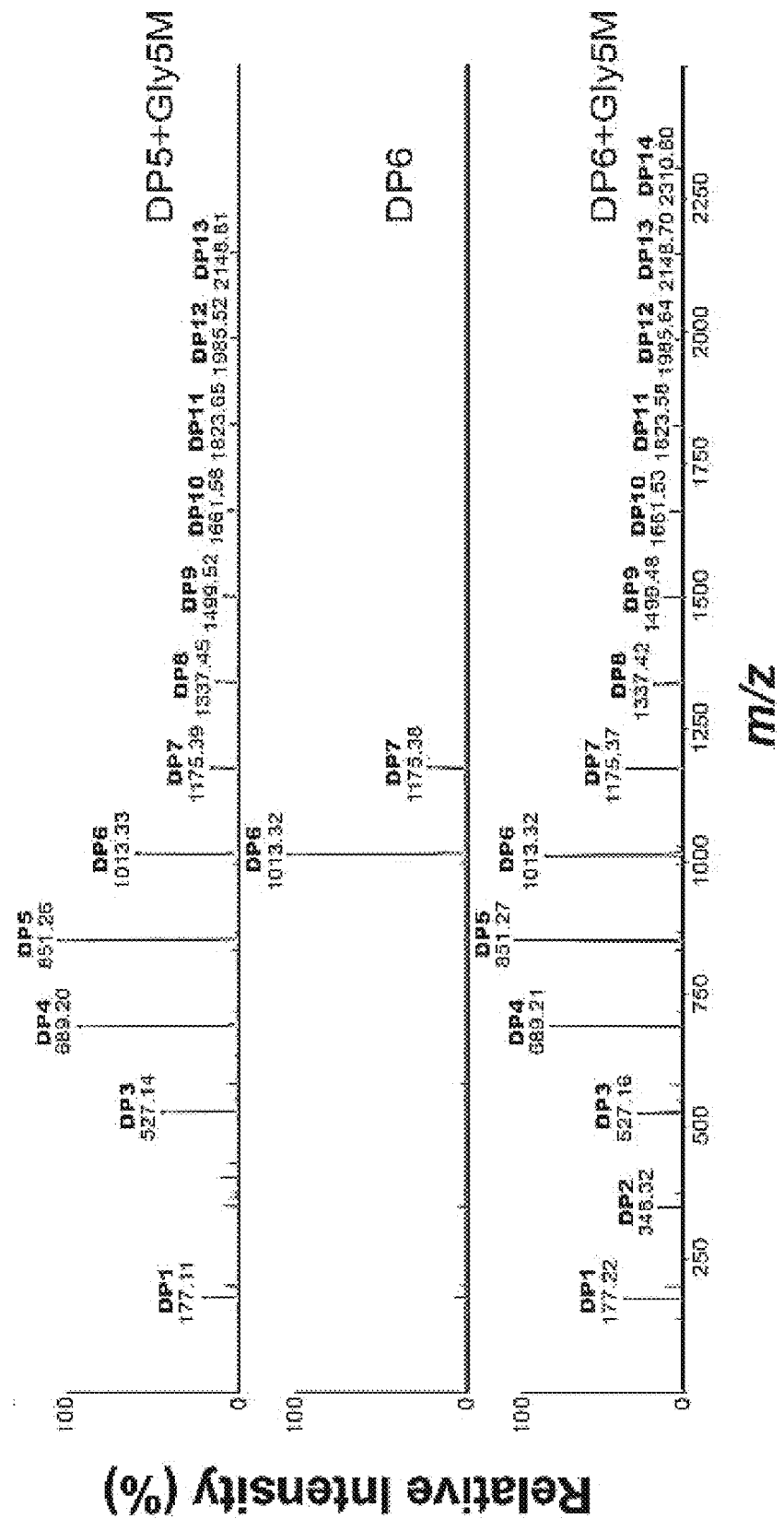

It was confirmed that, when pustulan was used as a substrate, it was confirmed that most of the substrate was converted into glucose, and other than glucose, various oligosaccharides ranging from DP2 to DP8 were produced (FIG. 8b).

When a laminarioligosaccharide (DP2 to 6) was used as a substrate, a peak indicating higher DP values than that of a specific substrate was identified, and therefore it was confirmed that, when the Gly5M protein was reacted with a laminarioligosaccharide (DP2 to 6), the Gly5M protein exhibited transglycosylation activity (see FIGS. 9 and 10a to c).

<Example 8> Analysis of Similarity and Phylogenetic Analysis of Gly5M Protein

According to similarity analysis using deduced amino acid sequences of different proteins deposited in GenBank, Gly5M consists of a GH5 catalyst domain and a carbohydrate-binding module 6 (CBM6) domain. For the hydrolysis of a β-1,3-glucan represented by laminarin, a β-1,3-endoglucanase (EC3.2.1.39), and a β-1,3-glucosidase or a β-1,3-exoglucanase (EC3.2.1.58) are needed. In each of GH16, GH17, GH55, GH64, GH81 and GH128, the β-1,3-endoglucanase requires at least two adjacent β-1,3-glycosidic bonds in its substrate. However, in the GH5, GH7, GH12, GH16 and GH17 families, a β-1,3-glucosidase or a β-1,3-exoglucanase (EC3.2.1.58) acts on the non-reducing end of a β-1,3-glucan to release glucose. GH5 is one of the largest GH families, previously known as the cellulase family A. To date, the amino acid sequences of 5,000 or more GH5 enzymes may be available in the CAZy database. Currently, GH5 contains 21 experimentally characterized enzymes with EC numbers, which include 19 GH5 enzymes derived from *Saccharophagus degradans* 2-40$^T$ (see Table 3). The GH5 enzymes share a standard mechanism by including a covalent glycosyl-enzyme intermediate. Therefore, the GH5 enzymes have both hydrolytic and transglycosylation activities. Until now, no enzyme of the GH5 family has not been known to exhibit β-1,3-endoglucanase activity. Gly5M belongs to GH5, and consists of a GH5 catalyst domain and a CBM6 domain. Gly5M in CAZy was predicted to be an endo-(1,3 or 1,4)-β-glucanase, and all 7 conserved amino acid residues of GH5 are present in Gly5M. *Saccharophagus degradans* 2-40$^T$-derived Cel5A, which is similar to Gly5M, consists of two GH5 catalyst domains and three CBM6 domains. However, the substrate specificity of Cel5A is not well known. The CBM6 domains serve as carbohydrate-binding modules (CBMs), and are widely present in cellulases. However, some of the CBMs bind to laminarin by presenting a specific ligand-binding surface recognizing the non-reducing end of 1,3-linked glucans such as laminarinases derived from *Bacillus halodurans* C-125 and *Streptomyces sioyaensis*. *Saccharophagus degradans* 2-40$^T$-derived Gly5L consists of a GH5 domain and a CBM6 domain, and exhibited β-1,3-endoglucanase activity like Gly5M. Since CBM6 is not found in any characterized β-1,3-exoglucanase in GH5, CMB6 will play an important role in imparting β-1,3-endoglucanase activity to GH5 enzymes.

Generally, the common broad specificity of a β-1,3-glucanase is the cleavage action on αβ-1,3-1,4-glucan through β-1,3-1,4-glucanase activity. However, such catalyst activity was not shown in Gly5M. Gly5M exhibited not only β-1,3-glucanase activity but also β-1,6-glucanase activity, and thus exhibited a rare broad specificity of the β-1,3-glucanase. In addition, Gly5M showed a relative activity of 55.6% with respect to a β-1,6-glucan and, pustulan, compared with laminarin. Gly5M effectively hydrolyzes pustulan to produce glucose and gentiobiose as main products. The Gly5M activity with respect to β-1,6-glycosidic bonds is much higher than that of any β-1,6-glucan-specific β-1,6-glucanase.

For phylogenetic analysis of the Gly5M protein, a phylogenetic tree was drawn by obtaining the genetic information of a β-1,3-endoglucanase derived from a previously known microorganism from the CAZy database (http://www.cazy.org).

Figure 11:
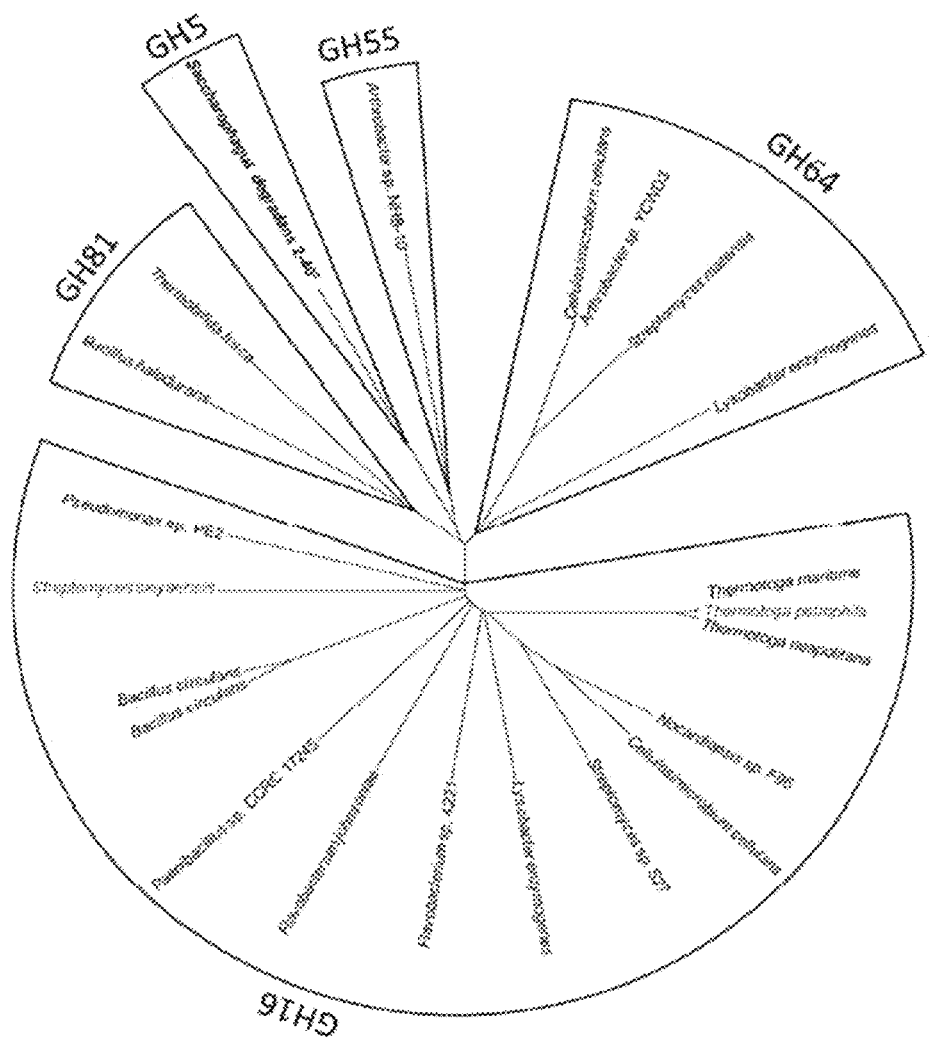
FIG. 11 illustrates the phylogenetic tree of a β-1,3-1,6-endoglucanase of the present invention.

As shown in FIG. 11, the Gly5M protein is the only β-1,3-endoglucanase found in GH5, which clearly shows a phylogenetic different from other previously known β-1,3-endoglucanases. GH5 enzymes are classified into 53 subfamilies, and Gly5M is classified as GH5_47. Gly5L has 44% similarity with Gly5M, and belongs to GH5_47. Therefore, it suggests that GH5_47 enzymes may serve as β-1,3-endoglucanases which exhibit novel activities with respect to the entire GH5.

In addition, it has been known that a glycoside hydrolase has transglycosylation activity as well as hydrolytic activity. Gly5M, in FIG. 11, exhibited transglycosylation activity with respect to β-1,3-oligosaccharides. Glucose is released from the non-reducing end of the substrate and then transferred to the 0-3 position of the substrate itself. Therefore, the substrate, a laminarioligosaccharide, may serve as a donor and an acceptor so as to form oligosaccharides with higher DPs than the substrate. For this reason, some β-1,3-1,4-endoglucanases may serve as a glucan synthase by transferring oligosaccharides with different DPs with respect to sugar receptors. *Euglena gracilis*-derived EgCel17A, which is a β-1,3-endoglucanase, catalyzes such transglycosylation, but ultimately, all intermediates were degraded into glucose, laminaribiose and laminaritriose. Gly5M seems to recognize a laminarioligosaccharide as both of the donor and acceptor in the synthesis of high DP β-1,3-glucan oligosaccharides. Generally, the enzyme-catalyzed synthesis of oligosaccharides is a useful method because it allows the selective synthesis of well-defined oligosaccharides without any protecting group. Therefore, Gly5M may be used as an oligosaccharide-producing catalyst.

As a result, it was confirmed that Gly5M serves as a β-1,3-1,6-endoglucanase with respect to laminarin and pustulan, as well as having transglycosylation activity. It was confirmed from the CAZy database that Gly5M is a novel glycoside hydrolase and present in GH5. When laminarin is used as a resource for fuels or functional oligosaccharides, Gly5M may be considered as a suitable enzyme for producing glucose and multiple laminarioligosaccharides.

TABLE 3

*Saccharophagus degradans* 2-40$^T$-derived GH5 enzymes

| Gene name | GenBank accession no. | Subfamily | EC no. of subfamily | Reference(s) |
|---|---|---|---|---|
| cel5A | ABD82260.1 | GH5_2 | 3.2.1.4, 3.2.1.32 | Aspeborg H et al., BMC Evol Biol 12: 186(2012.) |
| cel5B | ABD81750.1 | NCa | NAb | |

TABLE 3-continued

*Saccharophagus degradans* 2-40[T]-derived GH5 enzymes

| Gene name | GenBank accession no. | Subfamily | EC no. of subfamily | Reference(s) |
|---|---|---|---|---|
| cel5C | ABD79589.1 | GH5_4 | 3.2.1.4, 3.2.1.8, 3.2.1.73, 3.2.1.151 | Aspeborg H et al., BMC Evol Biol 12: 186(2012.) |
| cel5D | ABD81896.1 | GH5_4 | 3.2.1.4, 3.2.1.8, 3.2.1.73, 3.2.1.151 | Aspeborg H et al., BMC Evol Biol 12: 186(2012.) |
| cel5E | ABD82186.1 | NC | NA | |
| cel5F | ABD80834.1 | GH5_26 | 3.2.1.4, 3.2.1.73 | Aspeborg H et al., BMC Evol Biol 12: 186(2012.); Lafond M et al. J Biol Chem 291: 7183-7194(2016) |
| cel5G | ABD82496.1 | GH5_2 | 3.2.1.4, 3.2.1.32 | Aspeborg H et al., BMC Evol Biol 12: 186(2012.) |
| cel5H | ABD82494.1 | GH5_2 | 3.2.1.4, 3.2.1.32 | Aspeborg H et al., BMC Evol Biol 12: 186(2012.) |
| cel5I | ABD82675.1 | GH5_53 | 3.2.1.74 | Aspeborg H et al., BMC Evol Biol 12: 186(2012.) |
| cel5J | ABD81754.1 | GH5_2 | 3.2.1.4, 3.2.1.32 | Aspeborg H et al., BMC Evol Biol 12: 186(2012.) |
| gly5K | ABD82250.1 | GH5_46 | NA | |
| gly5L | ABD82253.1 | GH5_47 | 3.2.1.39 | The present invention |
| gly5M | ABD82280.1 | GH5_47 | 3.2.1.39 | The present invention |
| man5N | ABD79328.1 | GH5_8 | 3.2.1.78 | Aspeborg H et al., BMC Evol Biol 12: 186(2012.) |
| man5O | ABD79918.1 | GH5_8 | 3.2.1.78 | Aspeborg H et al., BMC Evol Biol 12: 186(2012.) |
| man5P | ABD79773.1 | GH5_7 | 3.2.1.25, 3.2.1.78 | Aspeborg H et al., BMC Evol Biol 12: 186(2012.) |
| man5Q | ABD81801.1 | NC | NA | |
| gly5R | ABD80383.1 | NC | NA | |
| gly5S | ABD81545.1 | GH_10 | 3.2.1.78 | Aspeborg H et al., BMC Evol Biol 12: 186(2012.) | aNC, not classified.
bNA, not applicable.

The enzyme of the present invention may be used in fields of producing oligosaccharides or glucose.

What is claimed is:

1. A method of producing an oligosaccharide or glucose, comprising:
reacting a β-1,3-1,6-endoglucanase represented by the amino acid sequences set forth in SEQ ID NO: 1 with one or more substrate selected from the group consisting of laminarin, pustulan and a laminarioligosaccharide.

2. The method according to claim 1, wherein the laminarioligosaccharide is any one of laminarioligosaccharides having degrees of polymerization of 2 to 6.

3. The method according to claim 1, wherein the reaction is performed at a temperature ranging from 20 to 45° C. and a pH ranging from 5 to 10 for 5 minutes to 1 day.

* * * * *

```
                        SEQUENCE LISTING

<160> NUMBER OF SEQ ID NOS: 4

<210> SEQ ID NO 1
<211> LENGTH: 869
<212> TYPE: PRT
<213> ORGANISM: Saccharophagus degradans 2-40T
<220> FEATURE:
<221> NAME/KEY: Saccharophagus degradans 2-40T
<222> LOCATION: (1)..(869)

<400> SEQUENCE: 1

Met Arg Glu Lys Leu Leu Arg Ala Leu Leu Thr Ser Ala Lys Phe Phe
1               5                   10                  15

Gly Ala Ser Leu Leu Leu Leu Ser Leu Phe Asn Leu Thr Ala Cys Gly
                20                  25                  30

Gly Gly Ser Ser Gly Thr Lys Pro Val Val Glu Glu Pro Gln Pro Glu
            35                  40                  45

Pro Gln Pro Glu Pro Glu Pro Glu Pro Glu Pro Glu Pro Glu Pro Glu
        50                  55                  60

Pro Glu Pro Glu Pro Gln Pro Glu Pro Glu Pro Glu Pro Asp Phe Ser
65                  70                  75                  80

Ala Leu His Thr Asp Gly Thr Lys Trp Val Asn Ala Asn Gly Asp Gln
                85                  90                  95
```

-continued

Val Leu Leu Lys Gly Val Asn Leu Gly Asn Trp Leu Leu Gln Glu Phe
            100                 105                 110

Trp Met Met Glu Gln Gly Ser Glu Asp Val Asn Asp Gln Cys Ser Leu
            115                 120                 125

Glu Ala Val Phe Asp Asp Arg Phe Gly Phe Ala Glu Arg Glu Arg Leu
        130                 135                 140

Met Asp Leu Phe Arg Asp Asn Trp Ile Asn Asp Arg Asp Trp Asp Ile
145                 150                 155                 160

Ile Ala Ser Phe Gly Met Asn Val Ile Arg Leu Pro Phe Ile Trp Asn
                165                 170                 175

Leu Ile Glu Asp Glu Asn Asn Pro Met Thr Leu Arg Asp Asp Ala Trp
            180                 185                 190

Gln Tyr Ile Asp Tyr Ala Ile Glu Gln Ala Glu Ala Arg Asp Met Tyr
            195                 200                 205

Val Ile Leu Asp Leu His Gly Ala Val Gly Ala Gln Gly Trp Glu His
        210                 215                 220

His Ser Gly Cys Ala Glu Leu Asn Glu Tyr Trp Gly Ser Glu Ala Tyr
225                 230                 235                 240

Gln Glu Arg Thr Arg Trp Leu Trp Gln Gln Val Ala Thr Arg Tyr Ala
                245                 250                 255

Asp Arg Asp Ala Val Ala Ala Tyr Gly Val Leu Asn Glu Pro Trp Gly
            260                 265                 270

Thr Thr Pro Glu Asn Leu Ala Val Glu Ala Ile Glu Leu Phe Asp Ala
            275                 280                 285

Ile Arg Glu Val Asp Ala Asp Lys Ile Ile Ile Leu Pro Gly His His
        290                 295                 300

Ser Gly Ile His Ala Tyr Pro Asn Pro Ala Thr Val Asn Gln Thr Asn
305                 310                 315                 320

Val Ala Tyr Glu Met His Phe Tyr Pro Gly Ile Phe Gly Trp Gly Glu
                325                 330                 335

Ile Gly Tyr Asp Val Asn Arg Asp Trp Leu Thr Cys Gly Pro Thr Gly
            340                 345                 350

Thr Ser Gly Val Cys Glu Trp Asp Ala Arg Leu Asp Ala Leu Asp Ser
            355                 360                 365

Pro Phe Leu Ile Gly Glu Phe Gln Pro Trp Thr Gly Leu Gly Pro Glu
        370                 375                 380

Leu Gly Ala Gln Ile Thr Arg Ala Thr Tyr Asp Thr Tyr Ala Ser Phe
385                 390                 395                 400

Asp Trp Ala Ser Thr Ala Trp Ser Tyr Lys Ile Ile Thr Ser Gly Gly
                405                 410                 415

Gly Gln Gly Gly Gly Thr Trp Gly Met Val Thr Asn Glu Arg Gly Leu
            420                 425                 430

Gly Leu Leu Ala Lys Ala Asp Thr Trp Ala Cys Ala Gly Trp Asp Ser
        435                 440                 445

Ser Phe Ala Asn Ala Cys Gly Val Ser Arg Thr Gly Phe Thr Pro Asp
450                 455                 460

Arg Glu Gly Glu Gln Thr Tyr Tyr Leu Val Ile Lys Phe Gly Ala Cys
465                 470                 475                 480

Cys Glu Gly Asn Leu Asp Ala Thr Leu Asp Ser Ile Ser Ile Ile Asp
                485                 490                 495

Asp Val Thr Gly Glu Glu Ile Ile Val Asn Gly Gly Phe Gly Ala Gly
            500                 505                 510

Thr Gly Trp Thr Glu Trp Tyr Glu Ser Ala Met Pro Ile Ile Asp Tyr

```
                515                 520                 525
Asn Tyr Thr Gly Ala Gly Val Pro Thr Gly Ser Asp Gly Ala Val Leu
        530                 535                 540
Arg Met Ser Gly Ala Ala Ala Ile Asn Gly Gly Val Tyr Gln Ala Ile
545                 550                 555                 560
Thr Leu Asp Ser Ser Lys Ser Tyr Ser Phe Ser Gly Val Phe Lys Asp
                565                 570                 575
Asn Gly Ser Ala Ser Ala Trp Ala Glu Ile Phe Leu Val Gln Ser Gln
        580                 585                 590
Pro Val Asp Gly Ser Asp Val Leu Ala Glu Gly Pro Phe Ala Ala Val
                595                 600                 605
Asp Phe Leu Thr Ala Pro Ile Glu Glu Ile Glu Asn Leu Phe Glu Ala
        610                 615                 620
Phe Gly Thr Thr Pro Tyr Asp Ile His Glu Glu Met Arg Ala Ala Met
625                 630                 635                 640
Thr Ala Glu Thr Ala Pro Thr Leu Phe Asp Leu Pro Gly Ala Pro Thr
                645                 650                 655
Gly Val Met Leu Ala Glu Asp Ala Gly Ala Ala Thr Ile Ser Trp Thr
        660                 665                 670
Ala Ser Gly Asp Ala Asn Val Thr Gly Tyr Asn Val Tyr Arg Ser Thr
        675                 680                 685
Ile Ser Gly Asn Ser Tyr Thr Leu Leu Ala Glu Asn Val Thr Ala Thr
        690                 695                 700
Thr Phe Val Asp Ser Thr Ile Asp Gly Glu Gln Thr Phe Tyr Tyr Thr
705                 710                 715                 720
Val Thr Ala Val Thr Asp Thr Ala Glu Ser Tyr Arg Ser Gln Glu Val
                725                 730                 735
Ala Thr Thr Phe Val Ala Val His Leu Pro Gly Lys Val Glu Ala Glu
                740                 745                 750
Ala His Ser Asp Met Met Gly Leu Gln Thr Glu Asn Thr Thr Asp Thr
                755                 760                 765
Gly Gly Gly Ile Asn Ile Gly Phe Ile Asp Ala Gly Asp Trp Phe Glu
        770                 775                 780
Tyr Glu Val Thr Ile Asp Thr Ala Ala Thr Tyr Asn Ile His Tyr Arg
785                 790                 795                 800
Leu Ala Ser Glu Pro Gly Ser Thr Gly Phe Thr Val Ser Ile Asn Asp
                805                 810                 815
Glu Val Leu Asn Thr Val Ala Val Pro Ala Thr Gly Gly Trp Gln Thr
                820                 825                 830
Trp Gln Thr Glu Ser Thr Thr Ile Thr Leu Pro Ala Gly Glu His Thr
        835                 840                 845
Leu Arg Phe Asp Ala Leu Gly Gly Gln Trp Asn Met Asn Trp Trp Ser
        850                 855                 860
Val Glu Ala Val Asp
865

<210> SEQ ID NO 2
<211> LENGTH: 2610
<212> TYPE: DNA
<213> ORGANISM: Saccharophagus degradans 2-40T
<220> FEATURE:
<221> NAME/KEY: Saccharophagus degradans 2-40T
<222> LOCATION: (1)..(2610)

<400> SEQUENCE: 2
```

-continued

```
atgagagaaa aactactgcg cgcactgtta acaagcgcca agttctttgg ggcgagctta      60
ctactgctta gcctatttaa ccttaccgcc tgtggcggag gctccagcgg cactaagccc     120
gtagtggaag agccacagcc agaaccgcag ccagaaccag aacctgaacc ggagccagaa     180
cctgaaccgg agccagaacc agaaccgcag ccagaaccag aaccagagcc cgacttctcg     240
gccctacata ccgatggcac taaatgggtt aacgccaatg gcgaccaagt gttgttaaaa     300
ggtgtgaacc tgggcaactg gctattgcaa gagttttgga tgatggagca aggctctgag     360
gatgtgaatg atcaatgctc cctcgaagct gttttttgacg accgctttgg ctttgctgag     420
cgcgagcgtc ttatggatct gttccgcgat aattggataa acgatcgcga ctgggacatt     480
atcgcctcgt tcggtatgaa cgttattcgc ctgccgttta tttggaacct aatagaagac     540
gaaaacaacc ccatgacact gcgtgacgat gcgtggcagt acattgatta cgccattgag     600
caggccgaag cccgcgacat gtatgtaatt ttagatttgc acggtgccgt aggggcacaa     660
gggtgggagc atcacagtgg ctgtgctgag cttaatgaat actggggtag cgaagcttac     720
caagagcgta cgcgctggtt gtggcagcaa gtggctacac gctatgccga ccgcgacgca     780
gtagcggctt acggcgtgct aaacgagccg tggggcacca caccagaaaa cctcgcagta     840
gaagccatcg aattattcga tgctattcgc gaagtggatg ccgacaaaat aattatttta     900
ccagggcacc actcaggtat tcacgcgtac cctaaccctg caactgtaaa ccaaaccaat     960
gttgcttacg aaatgcactt ttaccccggt attttttggtt ggggtgaaat aggctacgac    1020
gtaaaccgcg actggttaac ctgtggccca cgggcacca gcggcgtgtg cgaatgggat     1080
gcgcgcttag atgcattaga ttccccgttt taattggtg aatttcaacc gtggacaggc     1140
ctaggccccg aacttggtgc gcaaattaca cgtgccactt acgataccta cgcgagtttc     1200
gattgggcat ctacggcgtg gtcttacaaa attattacca gtggcggcgg tcaaggtggt     1260
ggcacatggg gcatggtaac aaacgagcgc ggtttaggtt tattggccaa agccgatact     1320
tgggcctgtg ccggttggga tagcagcttt gccaacgcat gtggtgtaag tcgcaccggt     1380
tttacgcccg atagagaagg cgagcaaacc tactatttag tgattaaatt cggcgcctgt     1440
tgcgaaggta acctcgatgc aacattagat agcatcagca ttatcgacga tgtaaccggc     1500
gaagaaataa ttgtgaatgg cggctttggt gctggtaccg gttggaccga gtggtacgaa     1560
agtgcaatgc ccattatcga ttacaactac accggtgcag gtgtgcctac gggtagcgat     1620
ggcgcggtgt tacgcatgag tggtgctgca gccattaacg gcggcgtgta ccaagctata     1680
acgttagatt ccagcaaaag ctatagcttc tctggtgtat ttaaagataa cggcagtgca     1740
agtgcatggg cagaaatatt cttagtgcaa agccagccgg ttgatggcag cgatgtatta     1800
gccgaaggcc catttgccgc ggtagatttt ttaaccgcac cgatagaaga aatagaaaat     1860
ctatttgaag cctttggcac taccccgtac gacattcacg aagaaatgcg tgcagccatg     1920
accgccgaaa cagcgccaac cttgtttgac ctgcccggcg cacctaccgg cgtaatgcta     1980
gccgaagatg caggcgcagc aacaataagt tggaccgcaa gcggcgatgc caacgtgact     2040
ggctacaatg tttatcgctc aacaatttct ggcaacagct ataccttgtt agctgaaaat     2100
gtaacagcta ccaccttcgt ggatagcacc atagatggcg agcaaacttt ctattacacc     2160
gtaacggctg taacagacac ggcagaaagc tatcgcagcc aagaggtagc cactaccttt     2220
gtagccgtgc atttacctgg caaagtagaa gcagaagctc atagcgatat gatgggctta     2280
caaaccgaaa acactaccga taccggcggc ggtattaata ttggctttat agatgccggc     2340
gattggtttg aatacgaagt aacaatcgat accgcggcga cctataacat ccactaccgc     2400
```

```
ttagcgagtg agccgggcag cacaggcttt accgtatcta taaatgatga agtgctaaat    2460
accgttgccg tacccgctac aggcggttgg caaacatggc aaaccgaaag tacaactatc    2520
accttacccg ccggcgaaca cacattgcgc tttgatgcat tgggtggcca gtggaatatg    2580
aattggtgga gtgttgaagc agttgactag                                    2610

<210> SEQ ID NO 3
<211> LENGTH: 31
<212> TYPE: DNA
<213> ORGANISM: Artificial Sequence
<220> FEATURE:
<223> OTHER INFORMATION: gly5m: forward primer
<220> FEATURE:
<221> NAME/KEY: gly5m: forward primer
<222> LOCATION: (1)..(31)

<400> SEQUENCE: 3
gcgggatcca tgagagaaaa actactgcgc g                                  31

<210> SEQ ID NO 4
<211> LENGTH: 48
<212> TYPE: DNA
<213> ORGANISM: Artificial Sequence
<220> FEATURE:
<223> OTHER INFORMATION: gly5m: reward primer
<220> FEATURE:
<221> NAME/KEY: gly5m: reward primer
<222> LOCATION: (1)..(48)

<400> SEQUENCE: 4
gcgctcgagg tggtggtggt ggtggtggtc aactgcttca acactcca                48
```